(12) United States Patent
Peter

(10) Patent No.: US 7,635,351 B2
(45) Date of Patent: Dec. 22, 2009

(54) DEVICE FOR METERED ADMINISTRATION OF A LIQUID PRODUCT

(75) Inventor: Daniel Peter, Niederwangen (CH)

(73) Assignee: Disetronic Licensing AG, Burgdorf (CH)

( * ) Notice: Subject to any disclaimer, the term of this patent is extended or adjusted under 35 U.S.C. 154(b) by 370 days.

(21) Appl. No.: 11/387,457

(22) Filed: Mar. 23, 2006

(65) Prior Publication Data

US 2006/0270987 A1  Nov. 30, 2006

(30) Foreign Application Priority Data

Mar. 24, 2005  (EP) .................................. 05006542

(51) Int. Cl.
*A61M 1/00* (2006.01)
*A61M 37/00* (2006.01)

(52) U.S. Cl. ................... 604/151; 604/155; 604/131

(58) Field of Classification Search ......... 604/151–155, 604/131

See application file for complete search history.

(56) References Cited

U.S. PATENT DOCUMENTS

| 5,106,375 | A |  | 4/1992 | Conero |
| 5,492,534 | A |  | 2/1996 | Athayde et al. |
| 5,582,591 | A |  | 12/1996 | Cheikh |
| 5,616,123 | A |  | 4/1997 | Cheikh |
| 6,423,035 | B1 | * | 7/2002 | Das et al. ..................... 604/155 |
| 6,485,465 | B2 | * | 11/2002 | Moberg et al. ............... 604/154 |
| 7,112,187 | B2 | * | 9/2006 | Karlsson ..................... 604/187 |
| 2003/0073954 | A1 |  | 4/2003 | Moberg et al. |
| 2004/0122366 | A1 |  | 6/2004 | Kazemzadeh |

FOREIGN PATENT DOCUMENTS

| DE | 41 33 402 C1 | 1/1993 |
| DE | 197 17 107 A1 | 11/1998 |
| WO | WO 2004/089448 A1 | 10/2004 |

* cited by examiner

*Primary Examiner*—Nicholas D Lucchesi
*Assistant Examiner*—Rebecca E Eisenberg
(74) *Attorney, Agent, or Firm*—Dorsey & Whitney LLP

(57) ABSTRACT

A device for administering doses of a substance, the device including a housing forming one of a product reservoir or a receiving seat for a product reservoir, a force sensor, a delivery mechanism which executes an axial output movement in a delivery direction to deliver a dose from the product reservoir, and which is supported via the sensor on the housing counter to the delivery direction, and a contact element on which the sensor is axially supported, at least one of the contact element and sensor forming a device for reducing play which, in an adjustment engagement with at least one of the housing or the delivery mechanism, is displaced into an adjustment position and axially secured in the adjustment position in such a way that axial play between the delivery mechanism and the housing is reduced.

27 Claims, 7 Drawing Sheets

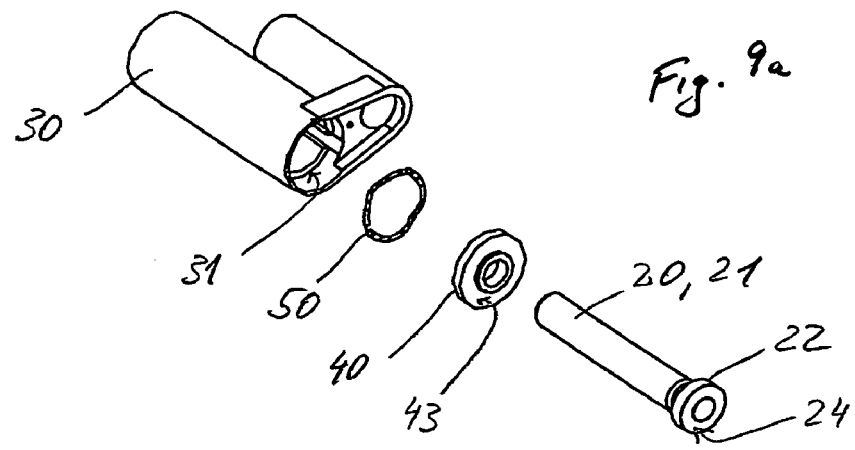
Fig. 9
Fig. 9a
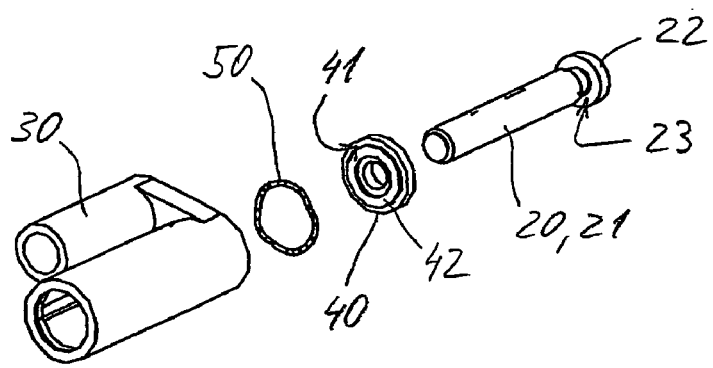
Fig. 9b
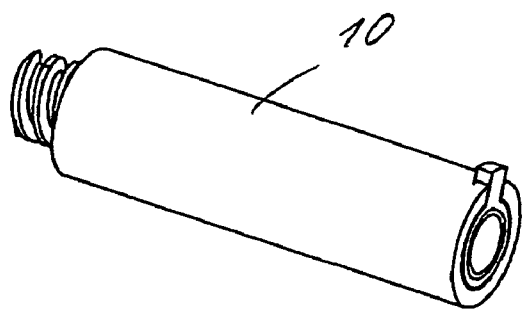
Fig. 10

DEVICE FOR METERED ADMINISTRATION OF A LIQUID PRODUCT

CROSS-REFERENCE TO RELATED APPLICATION

This application claims the benefit of German Application No. 05006542.4, filed on Mar. 24, 2005, the contents of which are incorporated in its entirety by reference herein.

BACKGROUND

The present invention relates to devices and methods for delivering, administering or dispensing substances, and to methods of making and using such devices. More particularly, it relates to devices and methods for metered administration of liquid products in biotechnology applications, preferably in medical applications, including veterinary and pharmaceutical applications. It relates in particular to infusion and injection appliances and devices, and methods of making and using such appliances and devices.

In various treatments, great importance is attached to the accuracy of the metering of products to be administered, for example in the administration of insulin in the treatment of diabetes. Infusion appliances and injection appliances are common in which a product to be administered is dispensed from a product reservoir by means of a motor-driven reciprocating piston pump in the case of infusion appliances or by means of a manually activated reciprocating piston pump in the case of injection appliances. In infusion appliances, the reciprocating piston is usually driven by a rotary drive mechanism, the rotation movement of the drive mechanism being converted by means of a spindle drive into the linear movement of the piston. In injection appliances, a spindle drive is often used for selecting the product dose to be administered, while the linear movement of the piston is effected directly by hand. In injection appliances, rack-and-pinion gears are also customary. A common feature of the above examples of appliances used for administration is that the accuracy of the metering depends critically on the degree of precision with which it is possible to predetermine the distance that the piston has to travel to deliver a defined dose of product.

Infusion appliances and injection appliances of the type mentioned above are described by DE 198 40 992 A, DE 198 22 031 C and DE 199 00 827 C, for example.

Particular demands on metering accuracy and precision have to be met by infusion appliances with which the product is often dispensed, delivered or administered over fairly long periods of time in small and discrete boluses or doses. Structural features serving in principle to improve the accuracy of the metering may at the same time also have a disruptive effect on, for example, the capacity for occlusion detection. An infusion appliance with advantageously configured, automatic occlusion detection is described in DE 198 40 992, to which reference is hereby made for the purposes of the present invention. A further appliance with occlusion detection is described in WO 01/72357 A2. For the occlusion detection, the entire delivery means is supported on the housing of the infusion appliance via a sensor. To ensure that this manner of support does not permit relative movements between the delivery means and the product container, WO 01/72357 A2 proposes, for assembly of the appliance, that the entire delivery means is first pressed in the delivery direction of the piston as far as an abutment formed by the housing, that the delivery means is then essentially relieved of the pressure, and finally that a closure cap is fitted into a rear opening of the housing and is adhesively bonded to the housing. The cap is intended to hold the delivery means in abutment against the housing. As an alternative configuration, it is also proposed that the delivery means, at its end remote from the piston, is supported on the rear base of the housing by means of an elastic sealing ring, and that a hollow space remaining between the rear face of the delivery means and the base of the housing is filled with a filler material, for example with silicone. The filler material should be substantially non-compressible, so as not to relieve the load on the sensor.

SUMMARY

It is an object of the present invention to deliver a desired dose of a product more accurately than before possible with known devices for metered administration of liquid products.

In one embodiment, the present invention comprises a device for administering doses of a substance, comprising a housing, a force sensor, a delivery mechanism and a contact element, at least one of the contact element and sensor comprising a device for reducing play between the delivery mechanism and the housing.

In one embodiment, the present invention comprises a device for administering doses of a substance, comprising a housing, a force sensor, a delivery mechanism which executes an axial output movement in a delivery direction and is supported via the sensor on the housing counter to the delivery direction, and a contact element on which the sensor is axially supported, at least one of the contact element and sensor forming a device for reducing play which, in an adjustment engagement with at least one of the housing or the delivery mechanism, is displaced into an adjustment position and axially secured in the adjustment position in such a way that axial play between the delivery mechanism and the housing is reduced.

In one embodiment, the present invention comprises a device for administering doses of a substance, the device including a housing forming one of a product reservoir or a receiving seat for a product reservoir, a force sensor, a delivery mechanism which executes an axial output movement in a delivery direction to deliver a dose from the product reservoir, and which is supported via the sensor on the housing counter to the delivery direction, and a contact element on which the sensor is axially supported, at least one of the contact element and sensor forming a device for reducing play which, in an adjustment engagement with at least one of the housing or the delivery mechanism, is displaced into an adjustment position and axially secured in the adjustment position in such a way that axial play between the delivery mechanism and the housing is reduced.

A device for metered administration of a liquid product, in accordance with one embodiment of the present invention, comprises a housing, a reservoir holding the product, and a delivery means. The housing can form the reservoir directly itself. In some preferred embodiments a container, for example an ampoule or the like, preferably forms the reservoir, however. The container is held by the housing in a defined position. Such a container may be inserted into the housing. As is already customary in the case of ampoules, the container can be prefabricated by being filled with a defined quantity of product and also by including a piston, that seals the rear of the container, already being received in said container. Prefabricated ampoules of this kind are customary for self-administration of insulin in treatment of diabetes. The product can be the aforementioned insulin, a growth hormone, and, in principle, any other medically active or, for example, cosmetically active product. In some embodiments, a device according to the present invention is preferably designed for self-administration.

The delivery means acts on the product located in the reservoir by executing an axial output movement in a delivery direction and thereby delivering product in metered quantities from the reservoir. In some embodiments, the delivery means is preferably of a multi-part design, for example so that a drive movement of a motor deviating from the output movement can be converted into the output movement.

To be able to automatically detect an occlusion or leakage, or both, in a part of the device through which the product flows, the device furthermore comprises a force sensor and a contact element which supports the sensor in or preferably counter to the delivery direction. The delivery means is supported via the force sensor on the housing counter to the delivery direction, such that the sensor picks up the reaction force necessary for generating the output movement and transmits it to the housing or another portion of the device. The sensor and the contact element form an interface between parts that are movable relative to one another for the purposes of occlusion and/or leakage detection, for example between the housing and the delivery means which is fully or partially axially movable relative thereto. Since, apart from negligible dissipation, the reaction force corresponds to the force required for generating the output movement, the measured value of the sensor can be used to draw conclusions regarding the fluid pressure of the reservoir, more precisely the differential pressure with respect to the environment. The fluid pressure or differential pressure increases when an occlusion occurs, and decreases when a leakage occurs, in relation to the fluid pressure corresponding to correct operation. By comparing the measured value with a reference value which, for example, corresponds to the ambient pressure or to an admissible maximum or minimum pressure in the reservoir, the occurrence of an occlusion or the occurrence of a leakage or both can be sensed, determined and/or assessed. As regards the physical parameter measured by the sensor, this parameter can be any parameter from which it is possible to determine the force taken up by the sensor. Any sensor that allows such a conclusion to be reached should be understood, within the meaning of the invention, as a force sensor. Thus, the sensor can be based on a strain measurement and accordingly be designed as a strain gauge. In some embodiments, the sensor is preferably flexurally elastic and is subjected to bending, for measurement purposes, for example in order to measure a strain. Distance measurement also permits the desired conclusion to be reached concerning the force or the fluid pressure and, consequently, an occlusion or leakage. Thus, for example, it is possible to measure an axial excursion of a sensor element which is axially movably supported, counter to an elastic restoring force, on the delivery means or the housing. Piezotransducers are another example of a force sensor. The force sensor does not have to be able to yield axially, although, in some embodiments, an axially yielding sensor is preferred for the measurement. As regards the occlusion and/or leakage detection and advantageous embodiments and configurations of the sensor, reference is made in particular, but only by way of example, to DE 198 40 992 A.

The fact that the delivery means is supported via the sensor has the effect that the delivery means is axially movable relative to the housing. Because of the axial mobility and the support via the sensor, there is a possibility of the bearing of the delivery means having an axial play. Because of the axial output movement of the delivery means, the metering accuracy would suffer in the event of an axial play in the bearing of the delivery means taking up the axial reaction force.

According to some embodiments of the present invention, a sensor, or preferably a contact element, forms a device for reducing play or, in other words, a device for tightening tolerances, increasing the closeness of complimentary or cooperating fit, and/or increasing precision. The device for reducing play is in an adjustment engagement, either with the housing, a structure associated therewith or the delivery means, in which it is displaced along a displacement path predetermined by the adjustment engagement into an adjustment position such that the axial play between the delivery means and the housing is reduced and preferably eliminated. In the adjustment position, it is secured against movements with an axial direction component. In some embodiments, the device for reducing play is preferably in the adjustment engagement with the housing predetermining the displacement path, since the device for reducing play, with such a design of the adjustment engagement, is in most application cases more easily accessible, as a result of which the adjustment, i.e., the displacement into the adjustment position, is made easier. In principle, however, the adjustment engagement can also be formed with the delivery means without compromising on functionality. For the sake of completeness, it should also be noted that both the contact element and also the sensor can each be in an adjustment engagement, namely one of these two elements with the housing, and the other with the delivery means, and both elements are displaced in coordination into an adjustment position and axially secured in their respective adjustment position such that an axial play between the delivery means and the housing is reduced and preferably eliminated. For the displacement into the adjustment position, the sensor itself can advantageously be used in order to measure an axial force during the displacement. In some embodiments, the adjustment position is preferably set by the displacement first being carried out as far as a position in which an axial force is measured by the sensor, then taking the displacement back a distance until the sensor establishes that no axial force is any longer acting on it.

In some preferred embodiments, a device for reducing play, in its adjustment position, is cohesively connected to the body with which its forms the adjustment engagement. The cohesive connection is preferably formed in the adjustment engagement.

In some embodiments the adjustment engagement is preferably a form-fit and force-fit engagement, for example a threaded engagement or the like.

In some embodiments, the adjustment engagement is preferably continuous in the sense that the axial play between the delivery means and the housing can be decreased continuously in the adjustment engagement, preferably to the value of zero, as is permitted for example by a threaded engagement. The threaded engagement also provides the advantage that the device for reducing play is axially supported by the adjustment engagement itself in each position it assumes along the displacement path. In some embodiments, the threaded engagement can be of a self-locking design, so that an additional cohesive connection for securing in the adjustment position is not absolutely necessary, although an additional cohesive connection, even when the adjustment engagement is designed as a threaded engagement, may be preferred as a means of securing the device for reducing play.

Since, by virtue of the present invention, the axial play is reduced by means of a displacement, i.e. an adjustment, of the device or associated with the mechanism for reducing play, it is readily possible, and is also preferred, in some embodiments, that the adjustment position of the device for reducing play is chosen such that a calibration curve of the sensor obtained by calibration remaining constant. The calibration curve is preferably not deformed by the reduction of axial play, and there is also preferably no zero offset. It would be ideal if the device for reducing play were adjusted such that the axial force acting on the sensor, apart from gravitational influences, is zero and the axial play is eliminated. In practice, the adjustment position of the device for reducing play may be preferably chosen such that a very slight axial play is still present, but this residual play, upon priming of the device, is practically or substantially completely cancelled out by the associated reaction movement of the delivery means. Alternatively, a residual axial force may be present in the adjustment position as long as the residual force is smaller than an axial force obtained through priming of the device. Priming of the device is understood as the removal of air from the product-conveying part of the device, such as is always carried out, for example, before product is dispensed for the first time from a replacement reservoir or refilled reservoir.

In one embodiment, the device for reducing play is preferably formed in one piece as a single adjustment member which is axially rigid in both adjustment engagements and at least to the extent corresponding to the axial play that is to be reduced. In the case of a multi-part device for reducing play, such a device for reducing play should be inherently axially rigid at least when it is secured in the adjustment position. Thus, for example, a two-part device for reducing play could have a first adjustment member which is in an adjustment engagement with the drive member, and a second adjustment member which is in an adjustment engagement with the output member. The two adjustment members would be displaced axially relative to one another into the adjustment position and, in the adjustment position, would be secured axially on one another or secure themselves automatically on one another in order to obtain the axial rigidity.

In a preferred development of the present invention, the housing of the device has a multi-part design and comprises a housing part, which preferably forms a shell of the device, and a support structure, which is supported on the housing part in and counter to the delivery direction. The housing part may preferably be a plastic part, preferably an injection-moulded part. The support structure may preferably be inserted into the housing part. The support structure supports the delivery means in and counter to the delivery direction. The support counter to the delivery direction is effected via the sensor and the contact element.

In a preferred embodiment, the delivery means is supported on a bearing body in and counter to the delivery direction. The support structure axially guides the bearing body and, together with it, the delivery means. In such embodiments, the axial play reduced or preferably eliminated by the device for reducing play according to the present invention is therefore the axial play between the support structure and the bearing body. Preferred embodiments also include one in which the support structure, at least in an axial section that supports the bearing body in and counter to the delivery direction, has an axial thermal expansion, measured in [m], which corresponds at least substantially to an axial thermal expansion of the bearing body. The bearing body is in one part or, if it is formed in more than one part, its several parts are connected rigidly to one another in and counter to the delivery direction, such that in this respect it is to be considered as a one-part body. The bearing body can be formed directly by the housing of the device. In some embodiments, it is preferable, however, if the bearing body is formed separately and is inserted into the housing. Preferred embodiments also include one in which the bearing body is a bearing sleeve which surrounds the drive member at least in one axial section.

The axial extent of the support structure may preferably be such that it supports a container, forming the reservoir, likewise in and counter to the delivery direction. Such a container can be formed as an ampoule, such as are known from the self-administration of medicines, for example insulin and growth hormones. Such ampoules are normally made of glass. The axial thermal expansion of the support structure, measured along the length of the container, preferably in an axial section that supports the container, should correspond or at least substantially correspond to the axial thermal expansion of the container.

In known administering devices, the product container is axially supported relative to the delivery means on a plastic housing. The usual materials for the container and the usual materials of the housings often have coefficients of thermal expansion that differ by a factor of 10. Correspondingly, the axial thermal expansions of housing and container in known devices also differ by a factor of 10 within the range of temperatures of use, which is between around $-20°$ C. and $+40°$ C. In the case of axial ampoule lengths of several centimeters, large differences of this kind in the axial thermal expansions of housing and container can appreciably impair the metering accuracy. Therefore, when it is stated herein that the axial thermal expansion of the support structure and the axial thermal expansion of the container are at least substantially identical, this is intended to signify that the axial thermal expansion of the support structure is nearer to the axial thermal expansion of the container than it is to the axial thermal expansion of the known housings. Accordingly, the axial thermal expansion of the support structure, measured over the axial section supporting the container, is nearer to the axial thermal expansion of the container than it is to that of conventional housings. Therefore, an axial thermal expansion of the support structure that differs from the axial thermal expansion of the container by not more than a factor of 5 is still to be regarded as a substantially identical thermal expansion. Preferably, the axial thermal expansions differ by not more than a factor of 3. In the simplest scenario, the approximation of axial thermal expansion can be achieved by the support structure being made from a material that has a coefficient of axial thermal expansion which, in the sense outlined above, corresponds at least substantially to the coefficient of thermal expansion of the container material. The coefficients of thermal expansion of the two materials, which can also be material mixtures, should likewise not differ by more than a factor of approximately 5, preferably by not more than a factor of approximately 3. It would of course be best if the coefficients of thermal expansion of the materials in question, in particular, however, the axial thermal expansions, were identical and the present invention comprises this ideal state. However, since in many embodiments, the container is preferably made of glass and the support structure is preferably a metal, this cannot be fully achieved. The lengths are compared by being measured at a temperature from the range of temperatures of use.

In a preferred multi-part embodiment, the delivery means comprises at least one drive member and at least one output member. The drive member may preferably be driven by motor if the device is an infusion appliance, and preferably manually if the device is an injection appliance, such that it executes a drive movement. The drive member and the output member are mechanically in engagement with one another such that the drive movement of the drive member produces an output movement of the output member. The output movement is or comprises an axial movement that is axially supported by the drive member. The axial movement can be superposed by another movement or by several other movements. However, in some embodiments, the output movement is preferably a purely linear axial movement.

In the output movement, the output member can act directly on the product located in the reservoir, for example by itself forming a reciprocating piston or by being connected permanently to a reciprocating piston. However, it can also simply press in a loose or abutting state against a reciprocating piston. A configuration is also possible in which the output member acts only via a transmission member or several transmission members on a delivery element, for example a reciprocating piston, which acts directly on the product when it executes the output movement. Thus, the delivery means can have a telescoping design, as is described in DE 197 17 107 A, to which reference is hereby made. In such a design, two adjacent telescope stages located in flank engagement in each case form a drive member and an output member according to the invention.

In some preferred administering devices in accordance with the present invention, the drive member is a rotation member which is mounted so as to move in rotation about a rotation axis. The output member is a translation member that can move in translation in a translation direction. A rotary drive movement of the drive member in a drive direction effects a translational output movement of the output member in the translation direction. If the administering device is an infusion appliance, the drive member that can move in rotation is preferably supported such that it cannot move relative to the reservoir, preferably relative to the housing, in and counter to the translation direction of the output member. Since the output member is supported in the flank engagement on the drive member during its translational movement, an undesired translational movement of the drive member would take place in reaction to the output movement of the output member, simply on account of the axial play that is unavoidable in the abovementioned rotary bearings and that affects its rotary bearing required for the rotation movement.

In a preferred development of the present invention, a further device for reducing play is therefore provided for delivery means of this kind, in order to reduce the axial play inherent to the rotary bearing of the drive member and, preferably, to eliminate it. The rotary bearing comprises the abovementioned bearing body which supports the drive member rotatably about its rotation axis.

In order to reduce the axial play of the rotary bearing, at least two axial support surfaces of the rotary bearing are connected axially rigidly to the bearing body, and at least two further axial support surfaces of the rotary bearing are connected axially rigidly to the drive member. In axially rigid connection, the support surfaces can be formed either directly by the bearing body or the drive member, or the support surface in question is formed by a separate body, which is then, however, connected axially rigidly, preferably completely rigidly, to either the bearing body or the drive member.

In a preferred embodiment of the present invention, at least one of the support surfaces is formed by the further device for reducing play which, in adjustment engagement either with the drive member or preferably with the bearing body, is moved into such an adjustment position and axially secured in the adjustment position on the bearing body or in the drive member in such a way that the axial play of the rotary bearing is reduced and preferably eliminated. Alternatively, the bearing body and the drive member can also be axially tensioned relative to one another by means of a spring, i.e. can exert an axial pressing force on one another. If the drive member and the output member are stages of a telescoping delivery means, as it is described in DE 197 17 107 A, for example, then the rotary bearing forms the rotary bearing of the first stage of the delivery means.

In some preferred embodiments, the engagement between the drive member and the output member is preferably a flank engagement which is formed by the drive member and the output member each having at least one engagement flank. Preferably, the at least one engagement flank of the drive member is formed directly on the drive member, and the at least one engagement flank of the output member is formed directly on the output member. The drive movement can be an axial movement, as may be the case especially when the device is an injection appliance. More preferably, however, the drive movement is a rotation movement, in this case particularly about an axis along which the output member executes the output movement.

For production reasons, flank engagements, such as are known from thread engagements and tooth engagements, have an axial play transverse to the engagement flanks, and this axial play may impair the metering accuracy, for example during a siphoning, i.e. during a suction situation, in the container.

In a preferred development of the present invention, therefore, a device for reducing play is provided which is in adjustment engagement, both with the drive member and also with the output member, in which the device for reducing play is moved relative to the output member and the drive member into an adjustment position and is secured in the adjustment position so that the axial play inherent to the flank engagement is reduced, compared to the known couplings based on flank engagement, or is preferably completely eliminated. The adjustment engagement with one of the two members, namely drive member and output member, corresponds to the flank engagement between the drive member and the output member. The other adjustment engagement defines the displacement movement of the play-reducing device along its displacement path. The length of displacement available in this adjustment engagement may preferably be sufficiently long that the device for reducing play, in its adjustment position, is not in abutment with the member in question but is still within the length of displacement available in this engagement. The two adjustment engagements can also be of the same kind or completely the same. In the latter case, they jointly define the course of the displacement path.

In some embodiments, the adjustment engagement with the drive member is preferably obtained with a form fit and force fit, and it is particularly preferably a thread engagement. The same applies as regards the adjustment engagement with the output member. Forming both the adjustment engagements of the second device for reducing play as thread engagements is expedient when the flank engagement between the drive member and the output member is also a thread engagement, as in some preferred embodiments of the present invention. However, it is also possible, for example, for the adjustment engagement that defines the displacement movement to be configured as engagement of an engagement member of the play-reducing device in a guide track purely with a form fit and, by means of an elasticity force, to form the other of the two adjustment engagements with a form fit and force fit. In preferred embodiments, the adjustment engagement defining the displacement movement is continuous or substantially continuous in the sense that the axial play between the drive member and the output member can, in the adjustment engagement, be decreased continuously from its production-related initial value to preferably a value of 0, as is permitted for example by a preferred thread engagement. The thread engagement provides the further advantage that the device for reducing play is axially supported by the adjustment engagement itself in each position assumed along the displacement path.

In preferred embodiments, the device for reducing play is secured on one of the members, namely drive member and output member, against axial movements relative to the member in question. The securing can be obtained by the device for reducing play moving along with the drive movement when the securing is between the drive member and the device for reducing play, and moving along with the output movement when the securing is between the device for reducing play and the output member.

In the illustrative case of a threaded engagement, the device for reducing play can be secured in the adjustment engagement in the adjustment position simply by self-locking. However, the device for reducing play may preferably be secured cohesively in its adjustment position in the secured adjustment engagement. This also applies if it is a thread engagement. The cohesive securing preferably takes place in the adjustment engagement with the drive member. However, securing on the output member would in principle also be possible with kinematic reversal. Instead of the securing being done only in one of the two adjustment engagements, the securing can also be done by the device for reducing play cooperating with the drive member and the output member, in this case preferably by the device for reducing play being elastically supported both on the drive member and also on the output member.

Preferred embodiments do not exclude the possibility that one of drive member and output member is a toothed rack and the other is a carrier engaging in the toothed rack. Such rack-and-pinion gears are known to those skilled in the art, for example from injection pens, so it is not necessary to go into details. For a rack-and-pinion gear of this kind, a device for reducing play can be formed by means of a further carrier, such that two carriers engage in the same series of teeth. In a rack-and-pinion gear of this kind, it is also possible to adjust the axial spacing of the two carriers in order to reduce the axial play that is present from the outset for tolerance reasons.

If the delivery means is able to telescope, a device for reducing play according to the invention is advantageously provided between each pair of telescope stages in flank engagement.

The thermal expansion of the delivery means, measured along the length between the bearing point of a drive member and a front end of a frontmost output member in its most forward position, and the thermal expansion of the support structure, measured along its axial section between the bearing point and the front end of the frontmost output member, should be at least substantially identical in the sense outlined above. If the delivery means comprises only a single output member, the measurement for the comparison is taken along the axial length to the front end of this output member.

BRIEF DESCRIPTION OF THE DRAWINGS

FIGS. 9a and 9b, shows components of the administering device in the illustrative embodiment of FIG. 6 in an exploded view, and FIG. 10 shows the translation member of the illustrative embodiment of FIG. 6.

DETAILED DESCRIPTION

Figure 1:
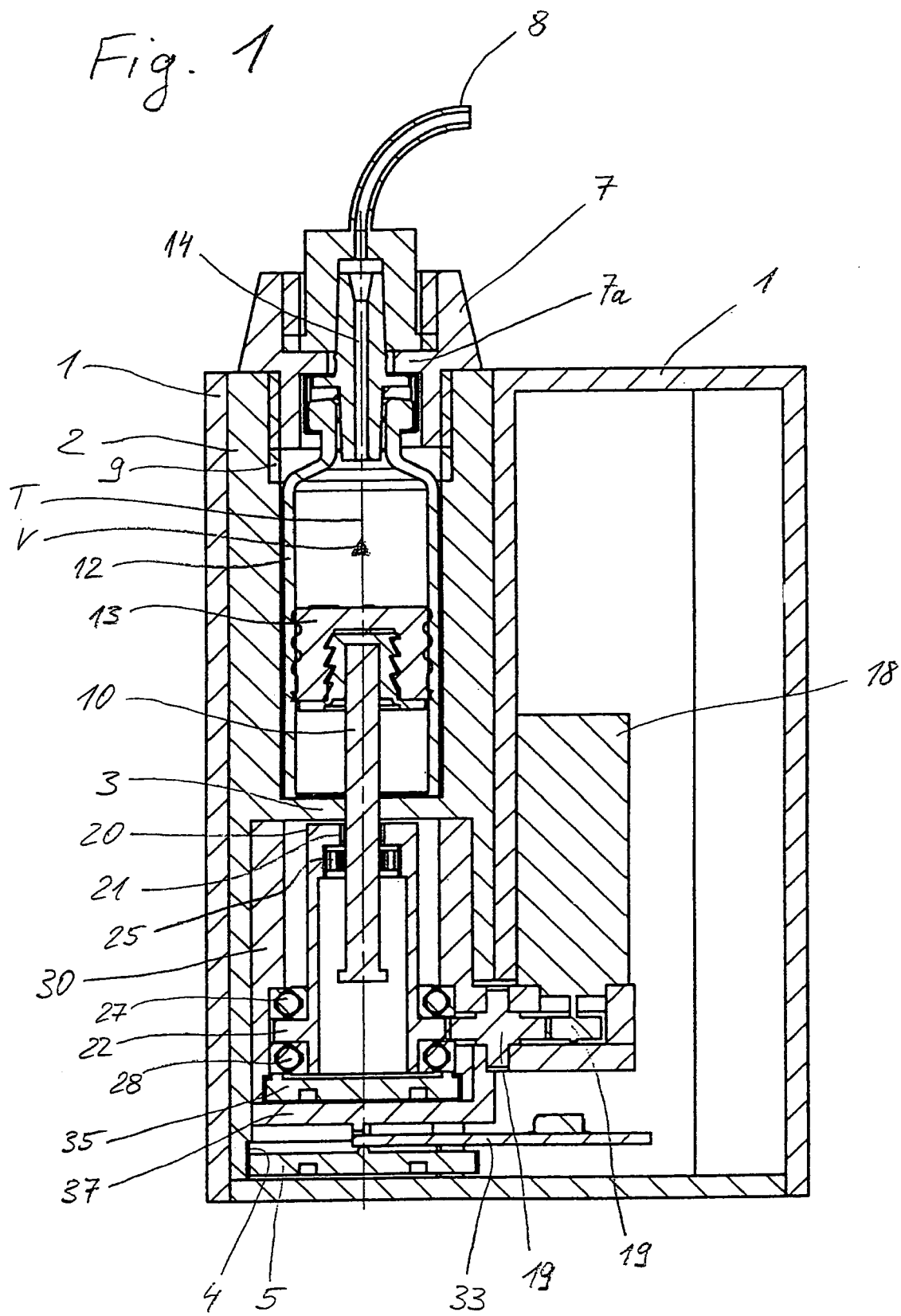
FIG. 1 is a longitudinal section through an administering device in one illustrative embodiment of the present invention.

An infusion appliance, representing an example of an administering device in accordance with the present invention, is shown in longitudinal section in FIG. 1. The appliance has a housing with a first housing structure 1, and with a second housing structure 2, a container 12 filled with an injectable product, and a delivery means or mechanism which functions to deliver or force the product in metered amounts from the container 12 and through an adjoining catheter 8 in order to administer it. The administration can take place subcutaneously in particular, as is customary in the treatment of diabetes, for example. The first housing structure 1 surrounds the second housing structure 2 and is designated below as the shell structure 1. The second housing structure 2 supports components of the infusion appliance and is designated below as the support structure 2.

At one end, which may be referred to as the front end, the container 12 has an outlet 14 via which the interior of the container is connected to the catheter 8. In the container 12, a piston 13 is received in such a way that it can move along a translation axis T in a delivery direction V towards the container outlet 14. The container 12 is open at its rear end. However, the piston 13 seals the container 12 off at the rear end.

The shell structure 1 forms a fixed shell in which the support structure 2, which is formed in one piece by a support body 2, is inserted and secured and forms a chassis of the housing. The shell structure 1 and the support body 2 substantially form the housing of the device. The support body 2 forms a first receiving space in which the container 12 is fitted, and a second receiving space for the delivery means. The container 12 rests with its rear free edge abutting against a radially inwardly projecting support web 3 of the support body 2 forming a support shoulder. The first receiving space formed by the support body 2 has, at the front end, an opening through which the container 12 is inserted. After insertion of the container 12, the opening is closed with a lid 7. The lid 7 is screwed onto the support body 2, which is provided with a thread 9 for this purpose. The support body 2 and the lid 7 could, however, each be provided with another engaging means for releasable engagement, for example with cooperating catches. The lid 7 also forms the connection element between the catheter 8 and the outlet 14 of the container 12. The lid 7 has, for the support shoulder of the support web 3, a counteracting support shoulder on a counteracting support web 7a which presses against a front edge of the container 12 and thus presses the container 12 in abutment against the support web 3 so that the container 12 is axially fixed relative to the support body 2. The lid 7 thus forms a front closure element 7a, and the support web 3 forms a rear closure element 3 of the first receiving space. The first receiving space is further shaped in such a way that the container 12 has the correct position and orientation in relation to the translation axis T. As a result, the support body 2 supports the container 12 axially in and counter to the delivery direction V with a form fit, i.e. by contact with the webs 3 and 7a serving as abutments. In a comparable way, the delivery means is supported axially between other abutments of the support body 2.

The delivery means comprises the piston 13, an output member 10, a drive member 20 and a motorized rotary drive. The output member 10 forms a translation member of the delivery means, and the drive member 20 forms a rotation member of the delivery means.

The output member 10 is a piston rod, e.g., a piston rod provided with a thread. In the illustrative embodiment, the output member 10 is provided with an outer thread 11 which can be seen in the longitudinal section in FIG. 2. The output member 10 extends through the support web 3 so that it protrudes into the first receiving space and the second receiving space of the support body 2. At its front end, the output member 10 is screwed onto the piston 13. The screw connection is established upon insertion of the container. The support web 3 guides the output member 10 linearly along the translation axis T. The support web 3 secures the output member 10 against twisting relative to the support body 2. In the illustrative embodiment, the thread 11 is for this purpose interrupted by at least one axial groove or flat in which the support web 3 engages.

The drive member 20 is arranged within the second receiving space of the support body 2. It is rotationally symmetrical with respect to the translation axis T. It is sleeve-shaped and can therefore also be designated as drive sleeve. At a front end of the sleeve, the drive member 20 forms a radially inwardly projecting web through which the output member 10 extends. On the inwardly projecting web, the drive member 20 forms an inner thread 21 which is in a threaded engagement with the outer thread 11 of the output member 10.

The drive member 20 is mounted such that it is rotatable about the translation axis T, but not axially movable relative to the support body 2. In a rear area, it has a radially outwardly projecting circumferential web 22 which is provided with an outer toothing. The drive member 20 is moved in rotation about the translation axis T via the outer toothing. Its rotary drive derives from a torque motor 18 which is accommodated in a further receiving space. The further receiving space is formed by the shell structure 1 and is separated from the two receiving spaces of the support body 2. The motor 18 drives the drive member 20 via a toothed gearing with radial teeth 19, of which an output toothed wheel 19 meshes with the outer toothing of the drive member 20. The threaded engagement between the drive member 20 and the output member 10 and the linear guiding of the output member 10 means that, when the drive member 20 is moved in rotation, its rotary drive movement results in an axial output movement of the output member 10 in the delivery direction V. The product displaced by the piston movement is dispensed through the catheter 8 and in this way administered.

Like any threaded engagement, the threaded engagement as such between the output member 10 and the drive member 20 is also associated with an axial play. The metering accuracy of the dispensing operation is therefore associated with a degree of imprecision, at least to the extent of this inherent axial play. For example, in the event of suctioning of the piston 13 on account of siphoning, or in the event of mechanical jolts or pressure differences between the housing interior and the environment, it can happen that the flanks of the outer thread 11 of the output member 10 lift from the driving thread flanks of the thread 21. The exact axial position of the piston 13 is therefore uncertain, to the extent of the axial play of the threads 11 and 21.

However, in accordance with the present invention, a device for reducing the play is provided which is formed by an adjustment member 25 and which virtually or substantially eliminates the axial play between the output member 10 and the drive member 20.

Figure 2:
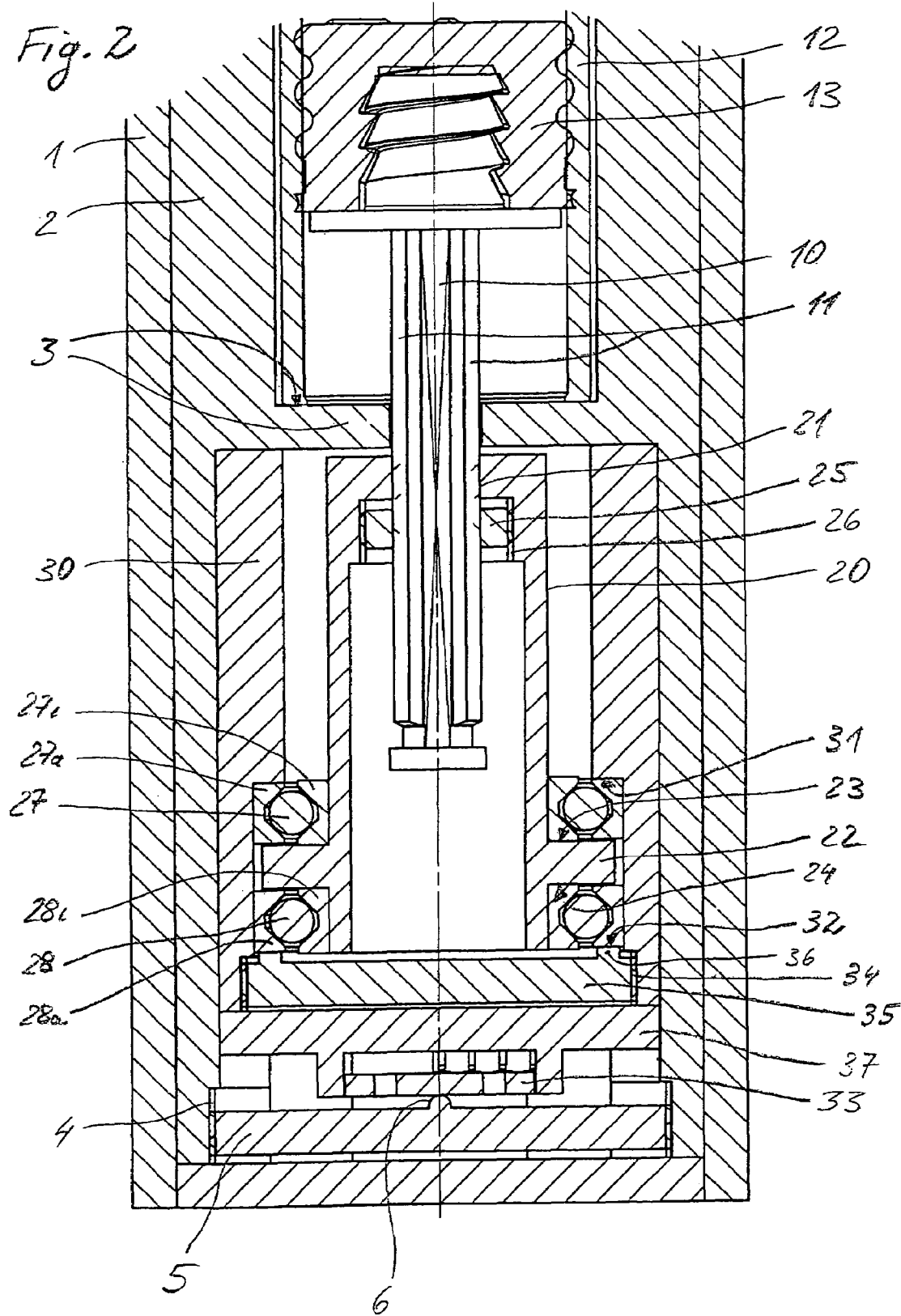
FIG. 2 shows part of the administering device of FIG. 1 in another longitudinal section.
Figure 3:
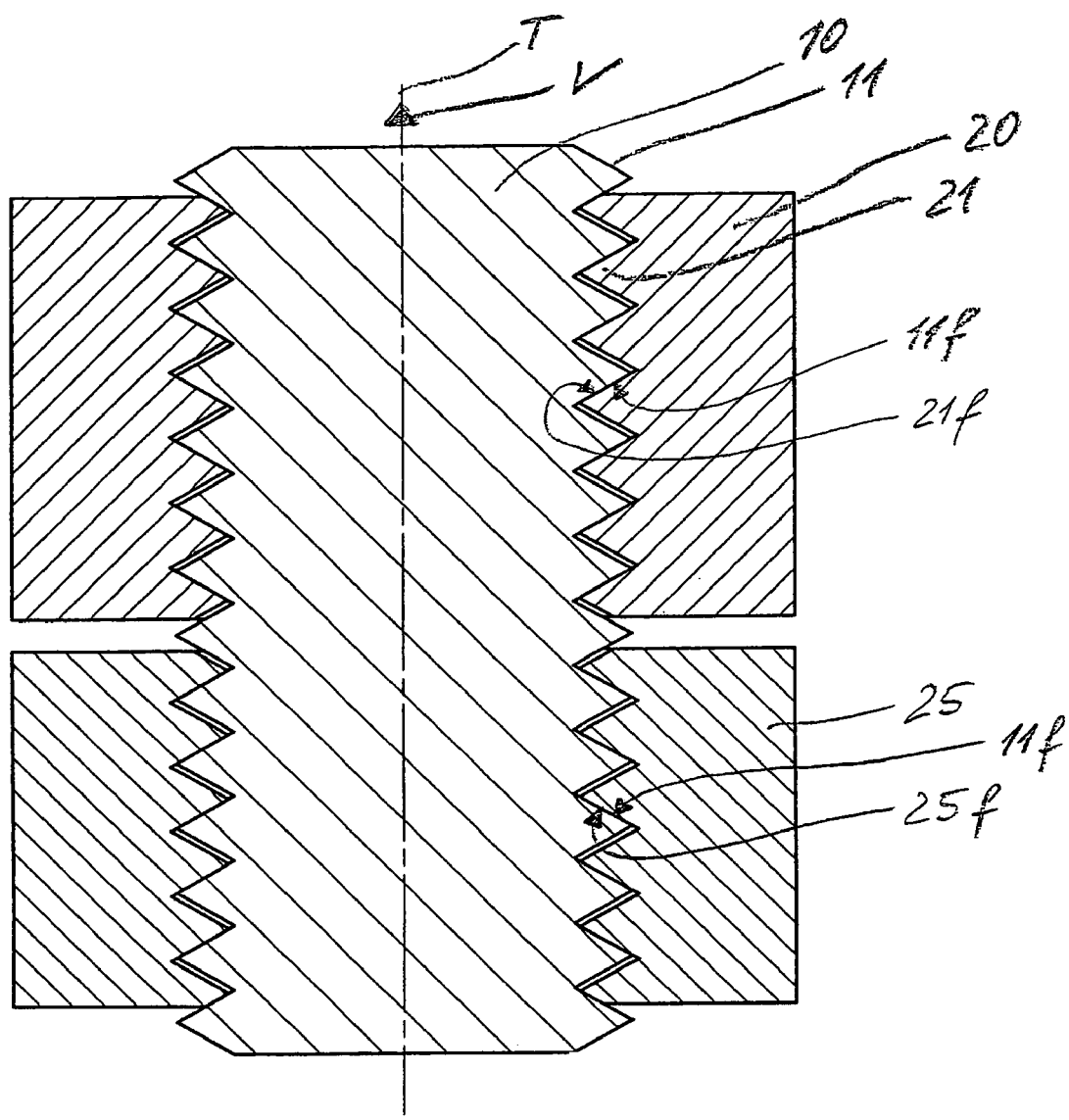
FIG. 3 shows an enlarged detail from FIG. 2.

The structure and action of the device for reducing play can be seen from FIGS. 2 and 3. The device for reducing play is formed by a one-piece adjustment member 25. The adjustment member 25 is in an adjustment engagement with the output member 10 and in a further adjustment engagement with the drive member 20. The adjustment member 25 and the two adjustment engagements are configured such that the axial play between the threads 11 and 21 is significantly reduced or eliminated.

In the illustrative embodiment, the adjustment member 25 is formed as a threaded nut with an inner thread and an outer thread. With its inner thread, the adjustment member 25 is in a threaded engagement with the outer thread 11 of the output member 10. With its outer thread, it is in a threaded engagement with an inner thread 26 of the drive member 20. The inner thread 26 is directed towards the outer thread 11 and formed axially immediately behind the thread 21. The inner thread and the outer thread of the adjustment member 25 lie at the same axial height, such that the adjustment member 25 can be axially thin and the device for reducing play can accordingly be made axially short, i.e., short along the translation axis T. The inner thread 26 may be sufficiently long that a secure adjustment engagement with the adjustment member 25 is ensured and the adjustment member 25 can additionally be displaced in this adjustment engagement such that the desired reduction of the axial play of the threads 11 and 21 can be provided. The inner thread 26 has a pitch allowing the adjustment member 25 to be displaced in threaded engagement with the inner thread 26 when threaded engagement exists between the threads 11 and 21 and between the thread 11 and the inner thread of the adjustment member 25.

FIG. 3 shows an enlarged representation of the threaded engagement of the threads 11 and 21 and the adjustment engagement between the thread 11 of the output member 10 and the inner thread of the adjustment member 25. The inner thread of the adjustment member 25 has the same pitch as the outer thread 11. In some embodiments, the pitch of the outer thread of the adjustment member 25 and of the inner thread 26 is preferably greater or smaller than the pitch of the threads 11 and 21, but so slight that the displacement of the adjustment member 25 in the adjustment engagement is possible.

For the reduction of axial play, the adjustment member 25 in its adjustment engagement with the output member 10 is set in such a way that its rear thread flanks 25f in relation to the delivery direction V are in contact with the front thread flanks 11f of the outer thread 11, while at the same time the front flanks 21f of the driving thread 21 are in contact with the rear flanks 11f of the thread 11 of the output member 10. For this purpose, the adjustment member 25 in its adjustment engagement with the drive member 20 is displaced relative to the drive member 20 counter to the delivery direction V until this state of flank contact is established. In this state, the adjustment member 25 is fixed on the drive member 20 and thereby secured. In an illustrative embodiment, the securing is produced adhesively by an adhesive agent being introduced into the adjustment engagement of the adjustment member 25 with the drive member 20. Other possibilities of cohesive connection between the adjustment member 25 and the drive member 20 are also conceivable, for example, sonic or laser welding in the adjustment position. If the inner thread 26, as in preferred embodiments, has a pitch different than the threads 11 and 21, the axial securing can be achieved by this alone or in combination with a cohesive connection. The adjustment position should be chosen such that the reduction in play causes no pressing forces, or at any rate no practically relevant pressing forces, to be exerted on the output member 10. The adjustment position is therefore chosen such that, in the threaded engagement of the threads 11 and 21, a very slight residual play remains, but one which is less or much smaller than the thread play inherent to this engagement alone, i.e. without reduced play.

In an illustrative embodiment, the adjustment position of the adjustment member 25 is chosen such that the thread 21 remains the driving thread of the drive member 20. The adjustment position could also be chosen, however, such that during adjustment the adjustment member 25 is moved against the rear thread flanks of the thread 11 and in this case the adjustment member 25 assumes the forward drive of the output member 10. Preference is given, however, to the adjustment position of the adjustment member 25 chosen for the illustrative embodiment and shown in FIG. 3.

Figure 4:
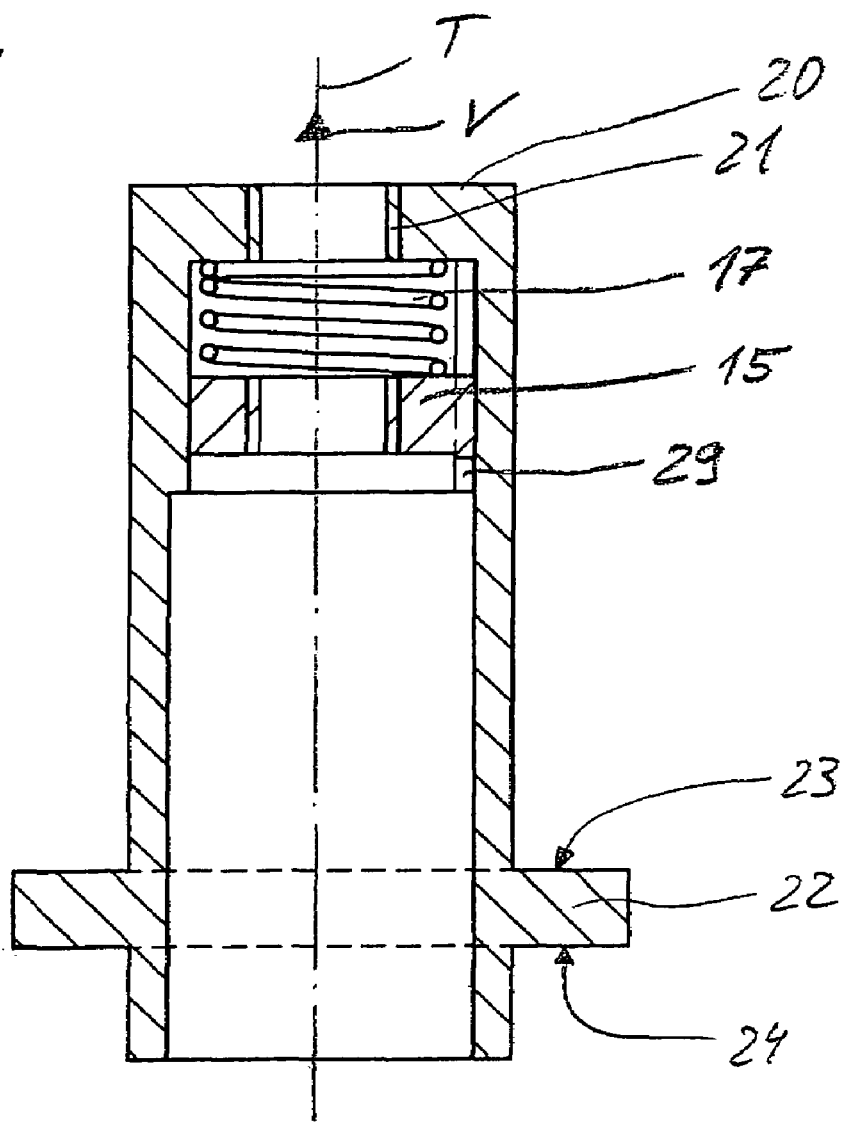
FIG. 4 depicts a device for reducing play in an alternative configuration.
Figure 5:
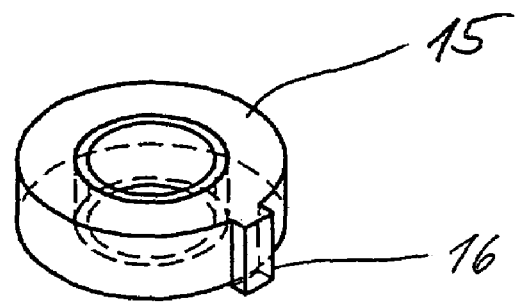
FIG. 5 shows an adjustment member of the device for reducing play from FIG. 4.

An alternative illustrative embodiment of a device for reducing play can be seen in FIGS. 4 and 5. Compared to the components of the illustrative embodiment in FIGS. 1 to 3, only the drive member 20 and the adjustment member, identified by 15 in the alternative illustrative embodiment, are modified, whereas the other components, in particular the output member 10, are unchanged. A further difference is that the alternative device for reducing play additionally comprises an elastic restoring element 17 in the form of a mechanical compression spring.

The adjustment member 15, like the adjustment member 25 before, is inserted into the sleeve forming the drive member 20. However, the adjustment member 15 is connected to the drive member 20 such that it is displaceable in an axially linear movement and is secured against twisting. The adjustment engagement of the adjustment member 15 with the drive member 20 therefore comprises a linear guide. The linear guide is formed by an axial, straight guide track 29 on the circumferential inner surface of the output member and by an engagement member 16 (FIG. 5) of the adjustment member 15 engaging in the guide track 29. The guide track 29 is limited in the delivery direction V by the radially inwardly projecting web of the drive member 20 that forms the driving thread 21. At the rear, the guide track 29 is open so that the adjustment member 15 can be pushed in. The restoring element 17 is also fitted beforehand. The restoring element 17 is supported in the delivery direction on the web of the drive member 20 forming the driving thread 21 and is supported counter to the delivery direction on the adjustment member 15. FIG. 4 shows this state before assembly with the output member 10.

For assembly, the adjustment member 15 is first inserted with the restoring element 17 into the drive member 20 into adjustment engagement with the guide track 29 and is pressed with a certain force against the restoring element 17. The output member 10 is then initially screwed onto the adjustment member 15 and then onto the driving thread 21. In the adjustment engagement, the rear thread flanks of the inner thread of the adjustment member 15 press with an elasticity force against those thread flanks of the thread 11 of the output member 10 that point in the delivery direction V. As a result, for the threaded engagement of the threads 11 and 21 via the two adjustment engagements of the adjustment member 15, the same state is obtained as is shown in FIG. 3. In the alternative device for reducing play, the adjustment member 15 is thus secured in the adjustment position by the elasticity force of the restoring element 17.

The infusion appliance in the illustrative embodiment has as a particular feature, but one known in principle from DE 198 40 992 A, an occlusion detection mechanism, which is also inherently subject to axial play, thus detracting from the metering accuracy. This inherent second axial play has its cause in the fact that the entire delivery means, in particular the output member 10 and the drive member 20, is supported axially on the support body 2 via a sensor 33. The sensor 33 is used to determine the force necessary for moving the piston 13 along the translation axis T. The sensor can, for example, be based on strain measurement. The sensor 33 is used to measure a physical parameter representing the liquid pressure in the container 12, in order to detect any occlusion or any leakage as early as possible during the administration of the product. As regards the occlusion detection and/or leakage detection and the sensor 33, the following deals only with those aspects concerning the axial play, and in other respects reference is made by way of example to DE 198 40 992 A.

For the occlusion detection and/or leakage detection function and/or mechanism, the delivery means, as has already been mentioned, is axially supported via the sensor 33. This means that the drive member 20, on which the output member 10 is axially supported in the driving engagement of the threads 11 and 21, is not connected in an axially rigid manner to the support body 2, but is instead mounted so as to be able to move axially relative to the support body 2, to be able to determine the liquid pressure in the container 12, or more precisely the differential pressure with respect to the environment. To obtain the axially movable bearing, the drive member 20 is mounted rotatably in a bearing body 30 and is axially secured on the bearing body 30. The bearing body 30 is inserted into the second receiving space of the support body 2 and secured against twisting. The support body 2 guides the bearing body 30 axially through sliding contact. The bearing body 30, and together with it the output member 10 and drive member 20, is supported axially on the support body 2 via the sensor 33 such that the sensor 33 picks up all the axial force acting between the bearing body 30 and the support body 2 and directed counter to the delivery direction V. In the delivery direction V, the bearing body 30 abuts against the support body 2. The bearing body 30 also supports the motor 18 and the gear 19 of the delivery means. In the illustrative embodiment, it is for this purpose provided with a lateral extension piece which projects through a lateral aperture of the support body 2 into the lateral receiving space of the housing shell structure 1, which lateral receiving space accommodates the motor 18, a control means and, if appropriate, a further appliance management system. For this purpose, the jacket of the substantially hollow-cylindrical support body 2 is provided with an aperture through which the sensor 33 also protrudes with a sensor attachment face at which it is connected to the control means and to a display.

The sensor 33 forms an elastic boom which is clamped firmly at both ends. The holder for the sensor 33 serves as an integrally formed sensor carrier 37 which is guided with axial sliding by the support body 2 and abuts, via a contact point 6 and the sensor 33, against the rear edge of the aperture of the bearing body 30 or if appropriate is fixedly connected to the bearing body 30. Since the sensor carrier 37 then also participates in each axial movement of the bearing body 30, if only abutment contact exists, it is attributed to the bearing body 30 and thus to the delivery means.

To substantially eliminate the axial play between the support body 2 and the bearing body 30, or at least to reduce it to an extent that can be tolerated in respect of the metering accuracy or that is no longer detectable in practice, a contact adjustment or compensation element 5 is provided which serves as an adjustment member 5. The adjustment member 5 forms the contact point 6 for the sensor 33. The contact point 6 comprises a cam which protrudes on the translation axis T from the front face of the adjustment member 5 in delivery direction V. The bearing body 30 is axially supported via the sensor 33 only in a quasi-punctiform manner at the contact point 6 on the translation axis T.

The adjustment member 5 is in an adjustment engagement with the support body 2. In the illustrative embodiment, this adjustment engagement is also a threaded engagement, namely between an inner thread 4 at the rear end of the support body 2 and a corresponding outer thread of the adjustment member 5. The adjustment member 5 is a circular cylindrical disc whose axial thickness is selected substantially exactly such that it is provided on its outer circumference with a sufficiently long threading for sufficiently secure adjustment engagement.

The adjustment position of the adjustment member 5 is chosen such that the bearing body 30 is in abutment against the support body 2 in the delivery direction, and at the same time the contact point 6 touches the rear face of the force sensor 33. The inner thread 4 of the support body 2 is sufficiently long to screw the adjustment body 5 in and to be able to adjust it in the adjustment engagement as far as this adjustment position. The adjustment position may preferably be chosen such that a calibration curve of the calibrated sensor 33 is not changed, in particular in such a way that the zero point of the calibration curve remains constant. The offset of the sensor 33 is therefore in other words "zero" when the pressure of the liquid in the container 12 corresponds to the ambient pressure. An offset is obtained upon priming of the infusion appliance. In principle, however, the adjustment position can also be chosen such that an offset is already obtained in the adjustment position before priming. This adjustment offset should be smaller than the offset obtained upon priming. The term "priming" designates the procedure by which the product-conveying parts, including an outlet point of the catheter 8 that can be formed by an insert cannula or a soft cannula, are filled completely with the product.

In its adjustment position, the adjustment member 5 is secured on the support body 2, in some preferred embodiments, cohesively connected to the support body 2. The cohesive connection can be obtained for example by laser welding or, in some preferred embodiments, by an adhesive agent introduced into the adjustment engagement.

Even without occlusion detection and/or leakage detection, an axial play is inherent not only to the threaded engagement between the output member 10 and the drive member 20, but also to the rotary bearings, such as are known from conventional infusion appliances.

To reduce the axial play in the rotary bearing of the drive member 20, adjustment or compensation is provided by an adjustment member 35. The adjustment member 35 is in an adjustment engagement with the bearing body 30. This adjustment engagement is also a threaded engagement. Like the adjustment member 5, the adjustment member 35 is also a flat, disc-shaped screw with an outer thread. At the rear end of the bearing body 30, the adjustment member 35 is screwed into the bearing body 30, which for this purpose forms an inner thread 34 in adjustment engagement with the outer thread of the adjustment body 35. The adjustment member 35 is arranged in such a way that, beyond the forces arising from the rotary bearing, no other external forces may act on the adjustment member 35.

For the axial supporting and securing of the drive member 20, the bearing body 30 forms a first support surface 31 oriented counter to the delivery direction V, and the adjustment member 35 forms a second support surface 32 facing towards the support surface 31. The drive member 20 forms, on its web 22, a third support surface 23 which is oriented in the delivery direction V and faces towards the first support surface 31, and a fourth support surface 24 which is oriented counter to the delivery direction V and faces towards the second support surface 32. A ball bearing 27 is held axially between the two support surfaces 31 and 23, and a further ball bearing 28 is held axially between the support surfaces 32 and 24. Each of the ball bearings 27 and 28 forms a radial bearing and, via the support surfaces 31 and 23 and also 32 and 24, an axial bearing. The ball bearings have, in the customary manner, an inner bearing ring and an outer bearing ring which are able to rotate relative to one another about the translation axis T and between which in each case a plurality of balls are arranged which transmit the radial and axial forces between the bearing rings. In the ball bearing 27, the inner bearing ring is indicated by 27*i* and the outer bearing ring by 27*a*. The ball bearing 28 correspondingly has an inner bearing ring 28*i* and an outer bearing ring 28*a*. The inner bearing rings 27*i* and 28*i* are radially supported on the outer circumferential surface of the drive member 20, and the outer bearing rings 27*a* and 28*a* are radially supported on the opposite inner jacket surface of the bearing body 30.

For the axial clamping of the ball bearings 27 and 28, the adjustment member 35, in its adjustment position, is pressed with a slight axial force against the outer bearing ring 28*a*. The adjustment member 35 and the ball bearing 28 are in contact only with the outer bearing ring 28*a* and the second support surface 32. The second support surface 32 is a circumferentially closed annular end face of an annular web 36 concentric to the rotation axis T, which annular web 36 protrudes in the delivery direction V from the front face of the adjustment member 35. The annular end face could also have interruptions. Similarly, the support surface 32 could be formed by individually protruding cams.

The outer bearing rings 27*a* and 28*a* have axially no contact with the support surfaces 23 and 24 of the drive member 20. The inner bearing rings 27*i* and 28*i* have axially no contact with the support surfaces 31 and 32. The axial force flow through the rotary bearing therefore runs exclusively via the contact of the support surfaces 31 and 32 with the respectively facing outer bearing ring 27*a*, 28*a* and the contact between the support surfaces 23 and 24 and the respectively facing inner bearing ring 27*i*, 28*i*. The axial force within the ball bearings 27 and 28 is therefore transmitted substantially exclusively by the balls. In this way, apart from manufacturing tolerances of the ball bearings 27 and 28, a rotary bearing is obtained which is virtually and/or practically free of play in the axial sense.

The adjustment member 35 is secured in its adjustment position like the adjustment members already described. The securing on the bearing body 30 is likewise preferably a cohesive connection and can in particular be effected by an adhesive agent which is introduced into the adjustment engagement. However, other cohesive connections, for example sonic or laser welding, or other suitable methods or structures, are also possible. As with the other adjustment members, the securing is effected in the adjustment engagement itself.

As regards the adjustment engagements, it should also be noted that the axial lengths of the paths of displacement of the adjustment members 5, 15, 25 and 35 in the adjustment engagements are each of such length that the respective adjustment member, when displaced into the adjustment position, cannot come into abutment contact against the body with which it is in the adjustment engagement, which blocks further displacement in the same direction.

In conventional infusion appliances and also in conventional injection appliances, a further source of axial play that detracts from metering accuracy is the large difference between the axial thermal expansion of the housings and the axial thermal expansion of the reservoir containers used. The housings are normally produced from plastic by injection moulding, while the containers are in most cases glass bodies. The coefficients of thermal expansion of these materials generally differ approximately by a factor of 10, i.e., a whole order of magnitude. For axial compensation of these differences in thermal expansion, the containers in the conventional appliances are supported on the housings with elastic resilience in the axial sense. In the temperature range in which the appliances are used, which range at least covers temperatures from about −20° C. to 40° C., the positions between the delivery means and the containers therefore change axially to an extent that has an appreciable effect on the metering accuracy.

This axial play, and its negative impact on metering accuracy, is countered by the support body 2 having, in the axial direction, a thermal expansion factor or capability, inherently or otherwise provided, which is much closer to the axial thermal expansion of the container 12 than is the case with the housings of conventional appliances. Thus, the support body 2 can be made from a material whose coefficient of thermal expansion differs by a factor of approximately 5 from the coefficient of thermal expansion of the material of the container 12. It is more preferable if the coefficients of thermal expansion are as close as possible to one another or even identical. Structural measures are also conceivable, for example manufacturing the support body 2 as a composite body which includes several materials within the composite, for example stiffening bodies that are embedded in plastic and that obstruct the thermal expansion of the plastic material in the axial direction. Preferred materials for obtaining favourable thermal expansion have a coefficient of thermal expansion of $30 \times 10^{-6}$/K or less in the temperature range in which they are used. The materials preferably have a thermal expansion that is uniform in all directions. However, a support structure in the form of a composite body will by nature have an irregular thermal expansion, relative to the whole composite body, so that in such a case only the axial thermal expansion and the coefficient of axial thermal expansion are meant.

Some of the preferred materials for constructing infusion appliances and injection appliances are listed in the following table, together with their coefficients of thermal expansion $\alpha$ in the temperature range within which they are used:

| Material | Coefficient of thermal expansion $\alpha$ in $10^{-6}$/K |
|---|---|
| Brass | 18 to 19 |
| Steel | 10 to 12 |
| Aluminium | 23 to 24 |
| Polyamide PA | 100 to 140 |
| Polyoxymethylene POM | 110 to 130 |
| Polyethyleneterephthalate PET | 70 |
| Polycarbonate PC | 70 |
| Polytetrafluoroethylene PTFE | 60 to 200 |
| Acrylonitrile/butadiene/styrene ABS | 80 to 110 |
| Glass | 5 to 10 |
| Hard rubber | 75 to 100 |

By means of a support body 2 or, more generally, a support structure 2 made, for example, of aluminium or an aluminium-based alloy, it is already possible to achieve a considerable improvement over those plastic materials which in terms of thermal expansion come closest to the container material, preferably glass, because the coefficient of thermal expansion of aluminium is smaller, approximately by a factor of 3, than the coefficient of thermal expansion of the plastic materials that come closest to the container material in terms of the coefficient of thermal expansion. A further improvement can be achieved by using a brass material. If the support structure is made of steel, or if it has steel components arranged in such a way that the axial thermal expansion is critically influenced by the steel components, it is even possible, in the most favourable case, to achieve an identical thermal expansion, with appropriate choice of the glass material. If the support body 2 or more generally a support structure 2, which of course also assumes an axial support function like the support body 2, is formed as a composite body, then stiffening bodies, for example axial fibres incorporated into a plastic matrix, can provide a comparably favourable thermal expansion behaviour, if the stiffening body or bodies have a thermal expansion as described above.

The multi-part design of the housing, in the illustrative embodiment the two-part design, can in principle even be dispensed with if the housing shell, in the illustrative embodiment the shell structure 1, has a thermal expansion according to the invention. In such a design of a housing shell, it is preferable if the housing shell is formed as a composite body, for example as a plastic matrix with embedded stiffening bodies, such as, in particular, axially oriented metal fibres or other suitable material.

Even though a support structure is already advantageous which only supports the container axially, it is more advantageous if such a support structure extends over the greatest possible length measured in the delivery direction V of the piston 13. The support structure, for example as the support body 2, should additionally provide axial support for the delivery means in both directions, too. It is also particularly expedient if the delivery means as a whole also has an axial thermal expansion as close as possible to the axial thermal expansion of the support structure, for example by the support structure and the components of the delivery means being made from the same material or, if appropriate, from different materials that have axial thermal expansions as close as possible to one another. Advantageously, the output member 10 or the drive member 20 has, or preferably both of these components have, substantially the same axial thermal expansion as the support body 2, i.e., a thermal expansion which differs at most by a factor of approximately 5 and preferably by less than a factor of 5, preferably by at most a factor of approximately 2 or even less, from the axial thermal expansion of the support body 2 and which is ideally identical.

The greater the axial length spanned by a one-part support structure or jointly by the several support bodies of a multi-part support structure, the smaller is the axial play attributable to different axial thermal expansions. Plastic parts of conventional type have to span very short axial lengths in this case. The shorter the axial lengths spanned by conventional plastic parts, the smaller is the axial play attributable to different thermal expansions. It is particularly expedient, as in illustrative embodiments of the present invention, if such a support body, or if appropriate several support bodies arranged axially in succession, is or are provided whose axial thermal expansion is close to that of the container and/or of the delivery means. The supporting means of the support body which secure the container and/or the delivery means axially on the support body or on the support bodies should be formed in one piece by the respective support body or be connected to the respective support body in such a way that they are not axially movable relative to the support body, such as, for example, by the pair of webs 3 and 7a, the pair comprising support web 3 and adjustment member 5, and the pair comprising adjustment member 35 and support surface 31.

The support body 2 is a comparatively simple sleeve body which is inserted into the shell structure 1 and is provided for the bearing of the mutually axially movable parts and thus for axial stiffening. The shell structure 1 itself can be produced in the customary manner from plastic by injection moulding. The shell structure 1 comprises two parts, namely a top part and a base part. The top part forms the receiving chamber for the support structure 2 and for those components of the administering device that are optionally not supported by the support structure 2. The base part is a simple plate which is connected fixedly to the rear face of the top part and there closes the receiving chamber.

In some embodiments, the lid 7 is preferably made from the same material as the support body 2. This also applies to the bearing body 30, the two adjustment members 35 and 5, and the carrier disc 37, resulting overall in a support structure that is very homogeneous in respect of the axial thermal expansion. The lid 7 and/or the carrier disc 37 and/or the adjustment member 35 and/or the adjustment member 5 may be produced from one of the customary plastic materials.

Figure 6:
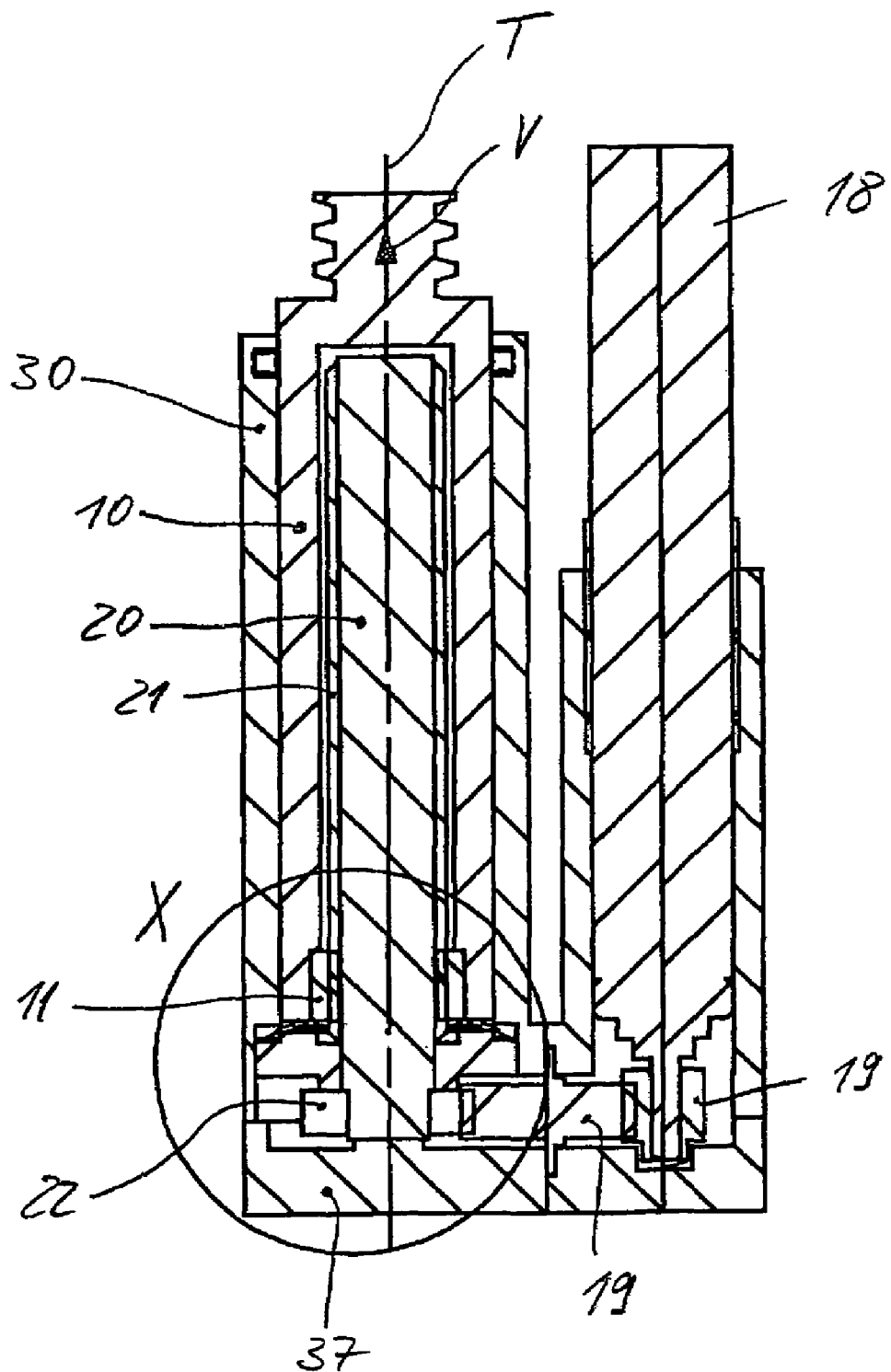
FIG. 6 is a longitudinal section through an administering device in another illustrative embodiment of the present invention.

FIG. 6 shows, in a longitudinal section, a bearing body 30 mounted in the same way as in the first illustrative embodiment, together with the components of an administering device that are supported by it, in accordance with a second illustrative embodiment, which is an infusion appliance. Those components of the second illustrative embodiment whose function and partly also whose construction are comparable with the components of the first illustrative embodiment have been given the same reference labels as in the first illustrative embodiment. Differences exist only in so far as are indicated below or as appear from the figures themselves. The statements concerning the first illustrative embodiment are intended also to apply to the embodiment of FIG. 6, unless anything is stated to the contrary.

The administering device in the second illustrative embodiment has a device for reducing play intended for eliminating or at least reducing the axial play between the rotation member 20 and the bearing body 30. In contrast to the first illustrative embodiment, the device for reducing play axially clamps the rotation member 20 directly against the sensor carrier 37. Moreover, in the second illustrative embodiment, the translation member 10 substantially surrounds the rotation member 20. The translation member 10 and the rotation member 20 are in threaded engagement with one another. For this purpose, the rotation member 20 is provided over most of its axial length with an outer thread 21, and the translation member 10 is provided with an inner thread 11 only at its rear end in relation to the direction of translation V. The translation member 10 is guided in an axially linear manner on the bearing body 30. As in the first illustrative embodiment, a motor 18, preferably an electric stepper motor, drives the rotation member 20 in a rotary movement about the rotation and translation axis T via a cylindrical gear with two toothed wheels 19 in radial engagement. For its drive, the rotation member 20 is again provided at its rear end with an outwardly toothed annular web 22 which is in radial engagement with the intermediate wheel 19 of the cylindrical gear for the rotary drive of the rotation member 20.

Figure 7:
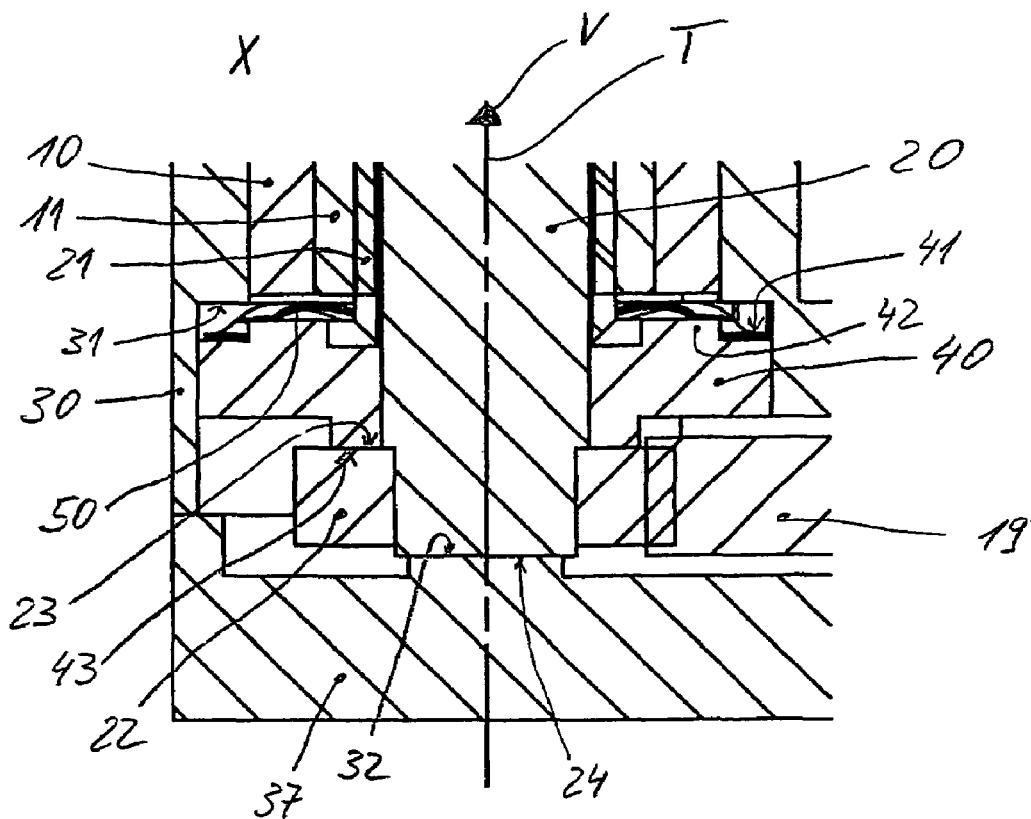
FIG. 7 shows a detail "X" from FIG. 6.

The rotary bearing of the rotation member 20 is shown in an enlarged view in FIG. 7. The rotary bearing in the second illustrative embodiment is formed as a simple slide bearing. The second support surface 32 of the sensor carrier 37 and the fourth support surface 24 of the rotation member 20 form a first slide pair surface of the rotary bearing. The two support surfaces 32 and 24 are in direct sliding contact with one another. The second support surface 32 is formed at the rear end of the rotation member 20. Protruding toward it from the sensor carrier 37, there is a short pedestal whose front face forms the second support surface 24. The pedestal frees the rotation member 20 from the sensor carrier 37. The formation of a pedestal permits more precise production of the second support surface 32. The third support surface 23 is formed in the manner of the support surface 23 in the first illustrative embodiment, namely by the front face of the annular web 22 that points in the translation direction T. The first support surface 31, facing axially towards it, is formed by the bearing body 30. However, the support surfaces 31 and 23 are radially offset from one another, i.e., they are not exactly in axial alignment. The radial offset is spanned by a transmission body 40, in the illustrative embodiment a transmission ring, which is arranged between the support surfaces 31 and 23. The transmission body 40 forms, on a front face, a front support surface 41 which lies in axial alignment opposite the first support surface 31 and which extends around the translation axis T and the rotation member 20, and it forms, on its rear face, a rear support surface 43 which lies in axial alignment opposite the third support surface 23. The rear support surface 43 is directly in abutment contact with the third support surface 23. A clear axial spacing remains between the first support surface 31 and the front support surface 41 facing towards it. An annular spring 50 is arranged between the two support surfaces 31 and 41 and bears axially on both support surfaces 31 and 41 with an axial pretensioning force.

Figure 8:
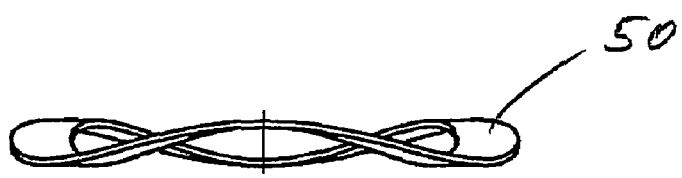
FIG. 8 shows a spring washer ring of a device for reducing play in the illustrative embodiment of FIG. 6, FIG. 9, including

The annular spring 50 is shown on its own in FIG. 8. It undulates about its perimeter and is made, for example, from spring steel. In the installed position, it bears alternately with its wave crests and wave valleys on the first support surface 31 and the front support surface 41 of the transmission body 40. Upon axial compression, it acts like a leaf spring.

As can be seen in particular from FIG. 7, the transmission body 40 not only serves to compensate for the radial offset, but also to centre the annular spring 50. For this purpose, the transmission body 40 is provided, on its front face, with an annular projection 42 about whose outer circumference the front support surface 41 extends, slightly set back axially.

The annular spring 50 and the transmission body 40 form the device or mechanism for reducing play in the second illustrative embodiment, since the transmission body 40 is axially movable relative to the bearing body 30. In some embodiments, the body is preferably guided in an axially linearly manner by the bearing body 30. In principle, however, it can move in rotation relative to the bearing body 30. Although the transmission body 40 can in principle be connected to the rotation member 20 in a manner fixed in terms of rotation, either by means of being joined thereto or by being designed in one piece with the rotation member 20, in some embodiments it is preferable if the transmission body 40, as in the illustrative embodiment, can move in rotation relative to the rotation member 20 and, even more preferably, is also axially movable. In this way, a further pair of slide surfaces of the rotary bearing is formed by the support surfaces 23 and 43 sliding directly on one another. The annular spring 50 is thus advantageously kept free from rotation movements.

In the second illustrative embodiment this provides, for the rotation member 20, an advantageously simple device for reducing play which, with sufficient pretensioning of the annular spring 50, eliminates any axial play between the rotation member 20 and the bearing body 30. In configurations in which the support surfaces 31 and 23 lie in axial alignment opposite one another, the transmission body 40 could be dispensed with. However, in order to keep the annular spring 50 free from rotation movements in these configurations too and/or to obtain an easy-to-produce centring for the annular spring 50 or also for another spring device generating the pressing force, the interposition of a transmission body in the manner of the transmission body 40 is then also of advantage.

FIG. 9, including FIGS. 9*a* and 9*b*, is an exploded view showing the bearing body 30, the rotation member 20, the transmission body 40 and the annular spring 50 in series along the imaginary translation axis, in a sequence suitable for one method of assembly in accordance with the present invention. FIG. 10 shows the translation member 10 on its own. In a first assembly step, the translation member 10 on its own can be inserted from behind into the bearing body, and the rotation member 20 can then be screwed into the translation member 10, or the threaded connection between the translation member 10 and the rotation member 20 can first be produced, and only then is the translation member 10 with the screwed-in rotation member 20 inserted into the bearing body 30. Before the rotation member 20 is screwed in, the transmission body 40 and the annular spring 50 are pushed via the outer thread 21 as far as the annular web 22 of the rotation member 20, after which the rotation member 20 is screwed into the translation member 10. After the translation member 10 and the rotation member 20 are arranged in the bearing body 30, the sensor carrier 37 is connected to the main part (shown in FIG. 9) of the bearing body 30 so that it closes the rear face of the bearing body 30 that is open for assembly purposes. The bearing body 30 and sensor carrier 37 are not movable relative to one another in the connected state. The connection is also configured such that the annular spring 50 is installed with a defined axial pretensioning force.

In the second illustrative embodiment, the threaded engagement of the threads 11 and 21 is formed as a simple threaded engagement, although, as in the first illustrative embodiment, it can also be readily formed to permit reduction of axial play by means of an additional device for reducing play.

It should also be noted that in the first illustrative embodiment a device for reducing or preferably eliminating axial play of the rotary bearing of the rotation member 20 can be formed as in the second illustrative embodiment, and that, conversely, the device for reducing play 35 based on the adjustment engagement can be provided in the second illustrative embodiment instead of the device for reducing play 40, 50. Combined forms are also conceivable. Thus, one of the roller bearings 27 and 28 could be arranged between one of the support surface pairs 31, 23 and 32, 24 or in each case one roller bearing between both support surface pairs, in which case the roller bearing or the two roller bearings would preferably each be arranged like the roller bearings 27 and 28 of the first illustrative embodiment, i.e., the annular spring 50 or an alternative spring would act only on one of the bearing shells of such a roller bearing.

Dispensing with the axially movable bearing and with the sensor 33, the bearing body 30 could be modified to form a housing with a seat for a reservoir 12 and could then serve directly as a shell structure, like the shell structure of the first illustrative embodiment. Such a shell structure can be formed like conventional housings. Alternatively, however, it can have the thermal expansion properties of the support structure 2 of the first illustrative embodiment, so that reference is made here to the explanations given in this connection with reference to the first illustrative embodiment.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for metered administration of a liquid product, said device comprising:
   a) a housing which forms one of a product reservoir or a receiving seat for a product reservoir,
   b) a force sensor,
   c) a delivery means which executes an axial output movement in a delivery direction in order to deliver product from the product reservoir, and which is supported via the sensor on the housing counter to the delivery direction, and
   d) a contact element on which the sensor is axially supported, wherein
   e) the contact element forms a device for reducing play which is axially movable in a threaded adjustment engagement with the housing from an initial position to an adjustment position in which an axial play between the delivery means and the housing is reduced, and whereby in the adjustment position the device for reducing play is secured against axial movement.

2. The device according to claim 1, wherein the securing in the adjustment position is effected by cohesive connection.

3. The device according to claim 1, wherein the delivery means, counter to an elastic restoring force of the sensor, is movable counter to the delivery direction relative to the housing.

4. The device according to claim 1, wherein the delivery means is mounted via the sensor to permit axial floating.

5. The device according to claim 1, wherein the sensor is calibrated and the adjustment position of the device for reducing play is chosen such that a calibration curve of the sensor obtained via the calibration remains constant.

6. The device according to claim 1, wherein the device for reducing play and the sensor have punctiform contact with one another.

7. The device according to claim 6, wherein the contact and the center of gravity of the delivery means are at least substantially in axial alignment.

8. The device according to claim 1, wherein the delivery means comprises a movably mounted drive member and an axially movably mounted output member which are in such engagement with one another that a drive movement of the drive member produces an axial output movement of the output member and in that the drive member and the output member are axially supported together on the housing via the sensor.

9. The device according to claim 1, wherein the delivery means comprises an output member, which executes the output movement, and a bearing body, on which the output member is supported counter to the delivery direction, and in that the bearing body is axially supported on the housing via the sensor.

10. The device according to claim 9, the delivery means further comprising a drive member which is mounted axially securely by the bearing body in such a manner as to turn about a rotation axis, and a motor for rotary driving of the drive member about the rotation axis, in that the drive member is coupled to the output member by means of threaded engagement, and in that the output member is guided axially relative to the housing.

11. The device according to claim 9, wherein the sensor is carried by a sensor carrier which is axially guided by the housing and follows the axial movements of the bearing body.

12. The device according to claim 1, wherein the housing comprises an axially rigid support structure which supports the delivery means in and counter to the delivery direction.

13. The device according to claim 12, wherein the support structure axially guides the delivery means.

14. The device according to claims 12, wherein the device for reducing play is in the adjustment engagement with the support structure.

15. The device according to claim 12, wherein the delivery means, in the delivery direction, is in abutment against the support structure directly or via one or more axially rigid components.

16. The device according to claim 12, the device further comprising a bearing body on which the delivery means is supported in and counter to the delivery direction, wherein the bearing body is axially supported on the support structure via the sensor, and wherein an axial thermal expansion of an axial section of the support structure supporting the bearing body in and counter to the delivery direction corresponds at least substantially to an axial thermal expansion of the bearing body.

17. The device according to claim 12, wherein the support structure supports a container, forming the reservoir, in and counter to the delivery direction.

18. The device according to claim 17, wherein the support structure, measured along the axial length of the container, has an axial thermal expansion that corresponds at least substantially to an axial thermal expansion of the container.

19. The device according to claim 17, wherein the axial thermal expansions compared to one another differ by at most 500%.

20. The device according to claim 12, wherein the delivery means comprises a drive member and an output member that projects axially into the container in the delivery direction, these members being in engagement with one another in such a way that a drive movement of the drive member effects the output movement executed by the output member, and in that the support structure, at least over an axial section extending from the engagement between the drive member and the output member to a front end of the output member in the delivery direction, has an axial thermal expansion corresponding at least substantially to the axial thermal expansion of the output member measured between the engagement point and the front end of the output member.

21. The device according to claim 20, wherein in an axial section extending from a bearing point of the drive member to the front end of the output member, the support structure has at least substantially the same thermal expansion as the delivery means, measured from the bearing point of the drive member to the front end of the output member.

22. The device according to claim 20, wherein the output member, from the engagement point to its front end, has, per unit of axial length, an axial thermal expansion corresponding at least substantially to the axial thermal expansion of the container measured per unit of axial length.

23. The device according to claim 1, wherein a housing shell structure surrounds the housing support structure.

24. The device according to claim 1, wherein the device for reducing play comprises a one-part adjustment member.

25. A device for metered administration of a liquid product, said device comprising:
   a) a housing which forms one of a product reservoir or a receiving seat for a product reservoir,
   b) a force sensor,
   c) a delivery mechanism which executes an axial output movement in a delivery direction in order to deliver product from the product reservoir, and which is supported via the sensor on the housing counter to the delivery direction, and
   d) a contact element on which the sensor is axially supported counter to the delivery direction, the contact element comprising a cam protruding from a front face of the thereof in a delivery direction, the cam forming a contact point between the contact element and the force sensor, wherein
   e) the contact element forms a device for reducing play which is axially movable in a threaded adjustment engagement with the housing from an initial position to an adjustment position in which an axial play between the delivery mechanism and the housing is reduced, and whereby in the adjustment position the device for reducing play is secured against axial movement, the delivery mechanism is in abutment against the housing in the delivery direction, and the contact point is in abutment against a rear face of the force sensor.

26. The device according to claim 25 wherein the threaded adjustment engagement comprises an engagement between an inner thread of a rear end of the housing and an outer thread of the contact element.

27. The device according to claim 25 wherein the contact element comprises a circular disc.

* * * * *

UNITED STATES PATENT AND TRADEMARK OFFICE
CERTIFICATE OF CORRECTION

PATENT NO. : 7,635,351 B2  Page 1 of 1
APPLICATION NO. : 11/387457
DATED : December 22, 2009
INVENTOR(S) : Daniel Peter It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 644 days.

Signed and Sealed this

Twenty-first Day of December, 2010

David J. Kappos
*Director of the United States Patent and Trademark Office*